United States Patent [19]

Tanner et al.

[11] Patent Number: 5,569,466
[45] Date of Patent: Oct. 29, 1996

[54] FILL COMPOSITIONS FOR SOFT ELASTIC GEL CAPSULES

[75] Inventors: Keith Tanner, Safety Harbor; Rickey S. Shelley, Largo, both of Fla.

[73] Assignee: R. P. Scherer Corporation, Troy, Mich.

[21] Appl. No.: 446,891

[22] Filed: May 17, 1995

[51] Int. Cl.⁶ .............................. A61K 9/48; A61K 9/66; A61K 9/64
[52] U.S. Cl. .......................... 424/452; 424/451; 424/455; 424/456; 424/460
[58] Field of Search .................................. 424/451, 452, 424/455, 456, 460

[56] References Cited

U.S. PATENT DOCUMENTS 4,935,243  6/1990  Borkan et al. ........................ 424/441

Primary Examiner—Carlos Azpuru
Attorney, Agent, or Firm—Banner & Allegretti, Ltd.

[57] ABSTRACT

A dosage unit form comprises a biologically active agent, such as a pharmaceutical, nutritional supplement or diagnostic, dissolved or suspended in a carrier liquid encapsulated in a soft elastic gel capsule. The carrier liquid comprises maltitol syrup as a major component. Maltitol syrup may be the only component of the carrier liquid, or may be blended with other liquids and/or excipients.

15 Claims, No Drawings

FILL COMPOSITIONS FOR SOFT ELASTIC GEL CAPSULES

BACKGROUND OF THE INVENTION

Field of the Invention and Description of the Prior Art

This invention is concerned with improvements in and relating to pharmaceutical compositions, nutritional supplements, and diagnostics. More particularly, it is concerned with such compositions in dosage unit form encapsulated in soft elastic gelatin (SEG) capsules.

Pharmaceutical compositions in dosage unit form encapsulated in SEG capsules are well known and generally consist of a fill material comprising one or more active agents dissolved or suspended in an appropriate liquid or paste vehicle, encapsulated in a soft gelatin shell, typically comprising gelatin together with a plasticizer. Manufacture of SEG capsules requires the fill material to be a pumpable liquid or paste. The carrier liquid can be a single or a multi-component system that must be compatible with the SEG capsule.

Liquids used in SEG capsules fall into two general categories, hydrophilic and lipophilic. There are many examples of acceptable lipophilic liquids used in the SEG format. Usually these are oils and are not water soluble. Due to the poor solubility of lipophilic liquids in water and gastric medium, they tend to have poor dispersion properties in the stomach, however. For this reason, formulations of pharmaceutical active ingredients and lipophilic carriers can retard the release of these active ingredients into the gastric fluid. It is often advantageous to prepare the active ingredients in solution for reasons of improved bioavailability and faster onset of action. Unfortunately, lipophilic liquids are poor solvents for many pharmaceutical active ingredients. These disadvantages can be overcome by using hydrophilic liquids.

There are few hydrophilic liquids suitable for use as carrier liquids in this application. The most versatile of these carriers in general use is polyethylene glycol, particularly in the molecular weight range of 200–800. This material offers good dispersion in gastric medium, excellent solubilizing capabilities for pharmaceutical active ingredients and good compatibility in the SEG format. However, there are disadvantages to using this material. One major disadvantage is that of instability; polyethylene glycol while in the presence of atmospheric oxygen reacts to form aldehydes. The residual aldehyde content of polyethylene glycol will react with the gelatin shell causing the protein polymers to inter- and intra-crosslink. The net result is a crosslinked gelatin shell that is insoluble in gastric media. To reduce this problem, polyethylene glycol must be handled in an inert atmosphere, for example, under a nitrogen blanket. Polyethylene glycol is also implicated as a potential irritant to mucous membranes found in the gastrointestinal tract.

Another class of hydrophilic liquids is non-ionic surfactants. These also have the disadvantage of being potential mucous membrane and stomach irritants. Common examples of materials in this category are polysorbate 80 and polysorbate 20. Legislation permits only small quantities of these materials to be ingested daily in over-the-counter and nutritional supplement products. This can restrict the use of these materials as a major component of a carrier system. A further disadvantage of non-ionic surfactants is that their inherent surface activity can have an adverse effect on the formation of the capsule seals, leading to a leaking product.

Sugar solutions are another category of hydrophilic carrier liquids. However, concentrated sugar solutions, such as glucose syrup, sorbitol solution and maltose syrup, are not particularly suitable for this application due to their adverse effect on gelatin capsules. Sorbitol causes excessive plasticization of the gelatin wall leading to deterioration of the capsule. Concentrated sugar solutions containing reducing sugars are also incompatible with gelatin. The reason is that the reactive aldehyde isomers of reducing sugars will cause gelatin crosslinking and unacceptable Maillard browning reactions. Common reducing sugars are dextrose and fructose which are present in glucose and maltose syrups. Also, concentrated aqueous solutions of sucrose are not sufficiently hygroscopic to retain water within an SEG capsule leading to distorted capsule shapes and crystalline sugar in the fill. Concentrated sugar solutions do have the advantage over previous examples of not being mucous membrane irritants, but some examples can cause some gastric disturbances due to their potential laxative properties when ingested in large amounts. This is particularly true of sorbitol.

U.S. Pat. No. 4,935,243 is directed to chewable, edible soft gelatin capsules with a shell of water, gelatin, plasticizer and hydrogenated starch hydrolysate, added to render the shell dispersible and soluble in the mouth. The SEG capsule contains a fill material with an active ingredient dispersed or dissolved in it. The hydrogenated starch hydrolysate in the capsule shell, which is used to augment the taste and chewability of the shell, is said to include hydrolysates "which contain less than 3% of polyols whose degree of polymerization (DP) is higher than 20, about 35–60% of maltitol (DP 2), about 0.1–20% of sorbitol (DP 1), and the balance being constituted by a mixture of polyols of DP 3–20."

U.S. Pat. No. 4,465,667 describes suspensions of aluminum hydroxide based antacid components in suspension form, stabilized with a hydrogenated hydrolysed glucose polymer in an amount of 2–30% by weight. Stabilizing agents disclosed include "a sugar alcohol [sic]as xylitol, mannitol, sorbitol or glycerol, by mixture of sugar alcohols obtained at the preparation of xylitol or a sugar such as glucose, maltose, fructose, or saccharose." Examples of specific stabilizing agents for the antacid suspension include LYCASIN®, the trademark for a syrup prepared by catalytic hydrogenation or reduction of a high maltose syrup obtained by the enzymatic hydrolysis of food starch. LYCASIN® is available from Roquette Corporation, Gurnee, Ill.

U.S. Pat. No. 2,580,683, issued Jan. 1, 1952, is directed to "a stable gelatin capsule inclosing an aqueous solution having hygroscopic material present in a quantity of a magnitude preventing deterioration of the capsule by the aqueous constituent of the solution."

SUMMARY OF THE INVENTION

Applicant has devised an alternative carrier liquid for active ingredients in SEG capsules which provides significant advantages as compared with the prior art carrier liquids described above. The invention utilizes maltitol [4-O-α-D-gluco-pyranosyl-D-glugitol]syrup to either dissolve or suspend pharmaceutical actives, nutritional supplements or diagnostics, which can then be encapsulated into soft gel capsules during the rotary die manufacturing process. Maltitol syrup can be the only component of the carrier medium or may be blended with other commonly used encapsulatable liquids and/or excipients. A sizable component should always be maltitol syrup.

Objects and advantages of the present invention include the following:

The invention provides good chemical stability for the capsule fill material. Unlike many non-hydrogenated concentrated sugar solutions, maltitol syrup is chemically very stable and therefore more compatible with drug systems.

As the carrier liquid for the active ingredient within SEG capsules, maltitol provides the advantage of compatibility with the SEG format. Maltitol syrup is hydrogenated glucose syrup and is compatible with SEG capsules. The hydrogenation process stabilizes the system; no reducing sugars are present. It is chemically more inert and is resistant to oxidation from atmospheric oxygen. Due to its chemical inertness, it will not cause gelatin crosslinking. Unlike many sugar solutions, Maltitol syrup is not prone to recrystalization of sugar components even at high concentrations.

Maltitol syrup offers favorable drug solubilities.

Maltitol syrup offers superior biocompatibility over many alternative fill materials in SEG capsules. The syrup does have some laxative properties, but is significantly less laxative than sorbitol syrup. Due to the low irritancy towards mucous membranes, it is ideally suited for suppository and vaginal applications where high doses of the carrier liquid are in intimate contact with sensitive tissues. Capsules designed for ingestion use can be either swallowable or chewable.

Maltitol syrup has a pleasant sweet taste and is often used commercially as a bulk sweetener. The sweetening power is similar to that of sucrose. This property can be used to prepare suspensions or solutions of actives that when combined with suitable flavors and excipients will produce palatable mixtures. Fill materials prepared in such a manner are ideally suited to chewable applications. Due to the sweet nature of maltitol syrup it helps to mask the flavor of certain unpalatable drugs. The dosage formats of the present invention can be ingestible, chewable, buccal, suppository, or vaginal types. The applications are in the field of human medicinal/nutritional supplements and diagnostics and veterinary applications.

Thus, maltitol syrup is a hydrophilic liquid suitable for use as a carrier liquid in SEG capsules which is both safe to use and compatible with the gelatin shell of the capsules. The invention contemplates a dosage unit form comprising a biologically active agent dissolved or suspended in a carrier liquid encapsulated in a soft elastic gelatin capsule, wherein the carrier liquid comprises at least about 20% maltitol syrup.

DESCRIPTION OF THE PREFERRED EMBODIMENTS

The invention provides SEG unit dosage forms that utilize the novel carrier medium, maltitol syrup. Maltitol syrup is a medium viscosity liquid, manufactured by hydrogenation of glucose syrup to produce sugar alcohols. It has been available commercially since the late 1950's. Inclusion of water in maltitol syrup is required to produce a mobile liquid and water is present in the syrup as commercially supplied.

Maltitol syrup can be formulated with many drugs and biological actives and diagnostic agents for use as a solution or a pumpable suspension. Pharmaceutical active ingredients may include, e.g., monograph drugs and proprietary drugs. Nutritional supplements in the maltitol carrier may include vitamins, active metabolites, minerals, and plant extracts, as well as other nutritional additives or agents. Diagnostic agents include radiolabelled biochemicals and other diagnostic tools. Biologically active agents suitable for use with the present invention include, without limitation, those selected from the group consisting of antihistamine formulations, analgesic formulations including non-steroidal antiinflammatory drugs (NSAID'S), antibiotics/antibacterials, antacid formulations, breath freshener formulations, allergy/sinus formulations, expectorants, sedatives, sore throat soothers, local anesthetics, laxative formulations, steroids, bronchodilators, prophylactic dental products such as fluoride or dentifrices, cough suppressants, vitamins, herbal extracts, motion sickness preventatives, antifungal formulations, anti-yeast formulations and diet aids. Maltitol syrup may also serve as a carrier for cosmetic and confectionery products.

The novel maltitol syrup carrier system may be used instead of or combined with other conventional liquids for one or more of the following reasons: 1) improved stability, 2) solubility, 3) greater biocompatibility, 4) improved dissolution, 5) legislative constraints, 6) novelty and 7) palatability. The major component (about 20% or greater) of the carrier liquid would always be maltitol syrup. Preferably, the maltitol has a solids loading of approximately 75% or 85%. Suspensions of active ingredients in maltitol syrup may benefit by containing rheological modifiers to prevent sedimentation. As noted above, the carrier system of the present invention comprises at least about 20% maltitol syrup. However, the benefits of the invention are particularly evident when the carrier system comprises at least about 50% maltitol syrup.

The inventive dosage forms may be used to administer biologically active agents both for human and animal consumption. For example, the novel liquid carrier system of the invention may be used in SEG capsules to provide prescription pharmaceuticals, over the counter drugs, nutritional supplements or diagnostics introduced orally, buccally, rectally, or by vaginal insertion in both human and veterinary applications.

Preparations of either solutions or suspensions of actives in maltitol syrup are prepared by the following methods:

1. Solutions

Maltitol syrup is dispensed into a suitable mixing vessel. Actives and solubilizing agents are added in sequence to the liquid and homogenized with high shear blending. If required, heat can be applied to the system to facilitate dissolution; normally temperatures in excess of 60 degrees centigrade are not required. The mixture once clear and free of particular matter is cooled and deaerated. During deaeration care must be taken to ensure that water loss is minimized; otherwise there may be an adverse effect on drug solubility.

Encapsulation of the liquid is performed on a standard rotary die encapsulation machine. Capsules are dried in low humidity conditions. Care must be taken not to over dry the capsules, as this could lead to deformed capsules due to excessive loss of water from the fill.

2. Suspensions

Maltitol syrup is dispensed into a suitable mixing vessel. Actives are added to the liquid and the mixture homogenized using high shear mixing techniques. Suspending agents if required are added to the system and depending on the nature of the material homogenized using the appropriate degree of shear. The mixture is deaerated; care is taken during this process to minimize any water loss. Capsules are manufactured using the rotary die encapsulation machine. Excessive drying of the capsules must be avoided.

Capsule size will be determined by the required potency of the active ingredient, the application and product aesthetics.

Examples of both solution and suspension fill formulations in maltitol syrup are provided below:

EXAMPLE 1

| Allergy Formulation | |
|---|---|
| COMPONENT | MG/SOFTGEL |
| Maltitol Syrup 75% | 719.0 |
| Pseudoephedrine Hydrochloride | 30.0 |
| Brompheniramine Maleate | 1.0 |
| Capsule Fill Weight | 750.0 |

EXAMPLE 2

| Antihistamine Formulation | |
|---|---|
| COMPONENT | MG/SOFTGEL |
| Maltitol Syrup 85% | 210.0 |
| Diphenylhydramine Hydrochloride | 50.0 |
| Capsule Fill Weight | 260.0 |

EXAMPLE 3

| Antacid Formulation | |
|---|---|
| COMPONENT | MG/SOFTGEL |
| Maltitol Syrup 75% | 434.0 |
| Calcium Carbonate | 540.0 |
| Simethicone | 20.0 |
| Polysorbate 80 | 6.0 |
| Capsule Fill Weight | 1000.0 |

EXAMPLE 4

| Chewable Antacid Formulation | |
|---|---|
| COMPONENT | MG/SOFTGEL |
| Maltitol Syrup 75% | 1401.0 |
| Calcium Carbonate | 1030.0 |
| Peppermint Oil | 4.0 |
| Sodium Crosscarmelose gum | 20.0 |
| Capsule Fill Weight | 2455.0 |

EXAMPLE 5

| Analgesic Formulation | |
|---|---|
| COMPONENT | MG/SOFTGEL |
| Lycasin 75% | 700.0 |
| Acetaminophen | 500.0 |
| Capsule Fill Weight | 1200.0 |

EXAMPLE 6

| Analgesic Formulation | |
|---|---|
| COMPONENT | MG/SOFTGEL |
| Ibuprofen | 200.0 |
| Lycasin 75% | 800.0 |
| Capsule Fill Weight | 1000.0 |

EXAMPLE 7

| Chewable Breath Freshener Formulation | |
|---|---|
| COMPONENT | MG/SOFTGEL |
| Lycasin 75% | 584.0 |
| Peppermint Oil | 3.0 |
| Polysorbate 80 | 3.0 |
| Capsule Fill Weight | 590.0 |

EXAMPLE 8

| Laxative Formulation | |
|---|---|
| COMPONENT | MG/SOFTGEL |
| Lycasin 75% | 966.7 |
| Senna Extract 60% A + B | 33.3 |
| Capsule Fill Weight | 1000.0 |

It should be understood that the foregoing disclosure emphasizes certain specific embodiments of the invention and that all modifications or alternatives equivalent thereto are within the spirit or scope of the invention as set forth in the appended claims.

I claim:

1. A dosage unit form comprising a biologically active agent dissolved or suspended in a carrier liquid encapsulated in a soft elastic gel capsule, wherein the carrier liquid comprises at least about 20% maltitol syrup.

2. The dosage unit form of claim 1 wherein the carrier liquid also contains at least one encapsulatable carrier liquid or excipient in addition to maltitol syrup.

3. The dosage unit form of claim 1 wherein the biologically active agent is selected from the group consisting of pharmaceuticals, nutritional supplements, diagnostics, cosmetics and confectionery products.

4. The dosage unit form of claim 1 wherein the biologically active agent is a pharmaceutical.

5. The dosage unit form of claim 1 wherein the biologically active agent is a nutritional supplement.

6. The dosage unit form of claim 1 wherein the carrier liquid formulated with the biologically active agent comprise a solution.

7. The dosage unit form of claim 1 wherein the carrier liquid formulated with the biologically active agent comprise a pumpable suspension.

8. The dosage unit form of claim 1 wherein the carrier liquid also contains a rheological modifier.

9. The dosage unit form of claim 1 wherein the soft elastic gel capsule is designed to be introduced by a mode selected from the group consisting of oral, buccal, rectal and vaginal insertion.

10. The dosage unit form of claim 1 wherein the biologically active agent is selected from the group consisting of analgesic formations, antihistamine formulations, antibiotics, antacid formulations, breath freshener formulations, allergy/sinus formulations, expectorants, sedatives, sore throat soothers, local anesthetics, laxative formulations, steroids, bronchodilators, prophylactic dental products, cough suppressants, vitamins, herbal extracts, motion sickness preventatives, antifungal formulations, anti-yeast formulations and diet aids.

11. The dosage unit form of claim 1 wherein the carrier liquid is a syrup obtained by catalytic hydrogenation or reduction of a high maltose syrup obtained from the enzymatic hydrolysis of food starch.

12. The dosage unit form of claim 1 wherein the carrier liquid comprises at least about 50% maltitol syrup.

13. The dosage unit form of claim 1 wherein the maltitol syrup has a solids loading of approximately 75%.

14. The dosage unit form of claim 1 wherein the maltitol syrup has a solids loading of approximately 85%.

15. The dosage unit form of claim 1 wherein the gel capsule is chewable.

* * * * *